United States Patent
Koch et al.

(10) Patent No.: US 8,070,735 B2
(45) Date of Patent: Dec. 6, 2011

(54) ASPIRATION PUMP UNIT

(75) Inventors: Urs Koch, Greppen (CH); Ivo Ramella, Ebikon (CH)

(73) Assignee: Medela Holding AG, Baar (CH)

( * ) Notice: Subject to any disclaimer, the term of this patent is extended or adjusted under 35 U.S.C. 154(b) by 326 days.

(21) Appl. No.: 12/300,051

(22) PCT Filed: May 3, 2007

(86) PCT No.: PCT/CH2007/000220
§ 371 (c)(1),
(2), (4) Date: Nov. 7, 2008

(87) PCT Pub. No.: WO2007/128156
PCT Pub. Date: Nov. 15, 2007

(65) Prior Publication Data
US 2009/0163882 A1    Jun. 25, 2009

(30) Foreign Application Priority Data

May 9, 2006   (CH) ..................................... 0749/06

(51) Int. Cl.
*A61M 1/00*   (2006.01)
(52) U.S. Cl. ........................................ 604/319; 604/317
(58) Field of Classification Search ................. 604/319; 220/500–557
See application file for complete search history.

(56) References Cited

U.S. PATENT DOCUMENTS

| | | | |
|---|---|---|---|
| 3,957,052 A | 5/1976 | Topham | |
| 4,883,476 A | 11/1989 | Kurtz et al. | |
| 5,421,252 A * | 6/1995 | Reichel | 100/193 |
| 5,507,734 A | 4/1996 | Everett et al. | |
| 5,800,004 A * | 9/1998 | Ackeret | 296/37.13 |
| 6,193,091 B1 * | 2/2001 | Olivetti | 220/23.88 |
| 6,352,525 B1 | 3/2002 | Wakabayashi | |
| 6,358,218 B1 | 3/2002 | Want et al. | |
| 6,394,996 B1 | 5/2002 | Lawrence et al. | |
| 6,708,607 B1 * | 3/2004 | Schwelling | 100/35 |

(Continued)

FOREIGN PATENT DOCUMENTS

DE    29911438 U1    12/2000

(Continued)

OTHER PUBLICATIONS

International Search Report from European Application 09012685 mailed Dec. 11, 2009.

(Continued)

*Primary Examiner* — Tatyana Zalukaeva
*Assistant Examiner* — Susan Su
(74) *Attorney, Agent, or Firm* — McDonnell Boehnen Hulbert & Berghoff LLP

(57) ABSTRACT

The portable aspiration pump unit of the invention, for the aspiration of bodily fluids, has a pump assembly housing (1) with a pump assembly (6) and at least one secretion or fluid collection reservoir (2) detachably connected to this pump assembly housing (1). The pump assembly housing has a front wall (11), a rear wall (10), and a side wall (16) arranged between these two walls, while the front wall and the rear wall each have one wall edge (100, 110) projecting beyond this side wall, and the fluid collection reservoir is held between these wall edges. In this way, the fluid collection reservoir can be secured easily to the pump assembly housing, yet be held firmly and protected inside it. This aspiration pump unit enables a simple and secure replacing of the fluid collection reservoir and affords the patient a heightened mobility.

16 Claims, 10 Drawing Sheets

U.S. PATENT DOCUMENTS

| | | |
|---|---|---|
| 6,962,301 B1 * | 11/2005 | Chang .......................... 241/100 |
| RE38,949 E * | 1/2006 | Wright et al. .................... 15/347 |
| 7,891,206 B2 * | 2/2011 | Yoon et al. ....................... 62/286 |
| 2002/0058915 A1 | 5/2002 | Wakabayashi |
| 2002/0161317 A1 | 10/2002 | Risk et al. |
| 2003/0163101 A1 | 8/2003 | Say |
| 2004/0024360 A1 | 2/2004 | Greter et al. |
| 2004/0111069 A1 * | 6/2004 | Schaaf et al. ................. 604/284 |
| 2005/0004534 A1 * | 1/2005 | Lockwood et al. ........... 604/304 |
| 2005/0171495 A1 | 8/2005 | Austin et al. |
| 2006/0036221 A1 | 2/2006 | Watson |
| 2007/0219532 A1 * | 9/2007 | Karpowicz et al. ........... 604/540 |

FOREIGN PATENT DOCUMENTS

| | | |
|---|---|---|
| EP | 1184043 A1 | 3/2002 |
| EP | 1219311 A2 | 7/2002 |
| GB | 2307180 A | 5/1997 |
| GB | 2378734 A | 2/2009 |
| WO | 96/05873 | 2/1996 |
| WO | 99/10024 | 3/1999 |
| WO | 03/016719 | 2/2003 |
| WO | 2005061025 A1 | 7/2005 |

OTHER PUBLICATIONS

International Preliminary Report on Patentability for PCT/CH2007/000220 mailed on Dec. 10, 2008.

* cited by examiner

ASPIRATION PUMP UNIT

CROSS-REFERENCE TO RELATED APPLICATIONS

The present application is a U.S. National Phase Application pursuant to 35 U.S.C. 371 of International Application No. PCT/CH2007/000220 filed May 3, 2007, which claims priority to Swiss Patent Application No. 00749/06 filed on May 9, 2006. The entire disclosure content of these applications are herewith incorporated by reference into the present application.

TECHNICAL FIELD

The invention concerns an aspiration pump unit and a fluid collection reservoir.

PRIOR ART

For the suctioning of bodily fluids or secretions from body cavities or wounds, stationary aspiration systems have generally been used in the field of medicine, especially for thoracic drainage. These aspiration systems basically consist of a suction source, especially a vacuum pump, a fluid or secretion collection reservoir, a surge tank arranged in between them, as well as connection lines, namely, a drainage line going from a patient to the secretion reservoir, a connection line going from the secretion reservoir to the surge tank, and a vacuum line connecting the surge tank to the suction source.

While these aspiration systems have proven to work well in practice, it is essential to the healing process, especially after surgery in the chest region, for the patient to be able to move and leave his or her bed as soon as possible.

Therefore, it has already been proposed to secure all the aforesaid components of the drainage system on a movable frame, so that the patient can gain a certain mobility, at least within the hospital.

Moreover, portable aspiration units are known, which substantially improve the mobility range of the patient. These portable aspiration units are used for the most part in wound drainage.

U.S. Pat. No. 6,352,525, however, discloses a portable pump unit which is said to be suitable for thoracic drainage. It can be fastened to the patient's body and thus allows him to move freely and relatively unimpeded. A vacuum pump, an energy source, a vacuum chamber and a secretion collecting reservoir are integrated in this drainage pump unit. The vacuum chamber is arranged in a first part, the secretion collecting reservoir in a second part and the vacuum pump in a third part. The first and third part in the working position are arranged above the second part and detachably joined to each other, as well as to the second part. Drainage connectors and vacuum connectors join the corresponding parts to each other. This device is relatively complex in construction and, what is more, it is not very easy to clean.

WO 99/10024 describes a portable pump unit for thoracic drainage, which is connected via an external line to an equally portable kidney-shaped secretion collecting reservoir. This device has the drawback that two separate units have to be carried, and what is more they are joined to each other via a hose.

In addition, EP-A-1,184,043 discloses a small-size aspiration pump, especially for wound drainage, which has a catchment reservoir for aspirated material and a cover, with all pump components essential to its working being integrated in the cover of the reservoir.

SUMMARY OF THE INVENTION

It is therefore one object of the invention to create a portable aspiration pump unit for the aspiration of bodily fluids, which affords the patient the greatest possible mobility and permits an easy attendance of the unit.

This object is fulfilled by a portable aspiration or drainage pump unit for the aspiration of bodily fluids and/or air, wherein the aspiration pump unit has a pump assembly housing with a pump assembly and at least one fluid collection reservoir detachably connected to this pump assembly housing, wherein the pump assembly housing has a front wall, a rear wall, and a side wall arranged between these two walls, wherein the front wall and the rear wall each have one wall edge projecting beyond this side wall, and the fluid collection reservoir is held between these wall edges wherein the fluid collection reservoir can swivel in and out between the wall edges.

The portable aspiration pump unit of the invention, for the aspiration of bodily fluids and/or air, has a pump assembly housing with a pump assembly and at least one secretion or fluid collection reservoir detachably connected to this pump assembly housing. The pump assembly housing has a front wall, a rear wall, and a side wall arranged between these two walls, while the front wall and the rear wall each have one wall edge projecting beyond this side wall, and the fluid collection reservoir is held between these wall edges. In this way, the fluid collection reservoir can be secured easily to the pump assembly housing, yet be held firmly and protected inside it.

The patient can carry the aspiration pump unit around with him or her in many different ways. He can hang it from his neck by a strap, fasten it to a belt, or wear it over the shoulder by a strap. If he is bedridden, he can place the unit on a table or simply hang it from the bed.

What is more, fluid collection reservoirs of different size can be used with the same housing. This allows one to lower the fabrication and operating expenses.

In one preferred embodiment, the fluid collection reservoir is held and can swivel in and out between the wall edges. Preferably, the reservoir is held and hinged in a lower region and can be locked to the pump assembly housing in an upper region.

Preferably, the reservoir can be removed entirely from the housing. Replacement of the reservoir is facilitated if the reservoir can be snapped into the housing.

The invented aspiration pump unit is used for medical purposes, especially for thoracic drainage and for wound drainage. However, other areas of application are possible, for example, for the aspiration of bodily fluids during surgery or for liposuction.

Especially in the case of thoracic and wound drainage it is beneficial for the device to remain in constant operation so that a permanent vacuum can be applied, which is actively maintained. Not only does this speed up the healing, but also it lowers the operating expenses, since the device is not used as long and therefore does not have to be rented for as long as the conventional device.

It is a further object of the invention to create a fluid collection reservoir which can be used in particular for aspiration pump units of said type and which prevents contamination of the suction line or of the suction pump with aspirated fluid.

BRIEF DESCRIPTION OF THE DRAWINGS

The object of the invention shall be explained hereafter by means of preferred sample embodiments, which are represented in the enclosed drawings. These show.

WAYS OF IMPLEMENTING THE INVENTION

Figure 1:
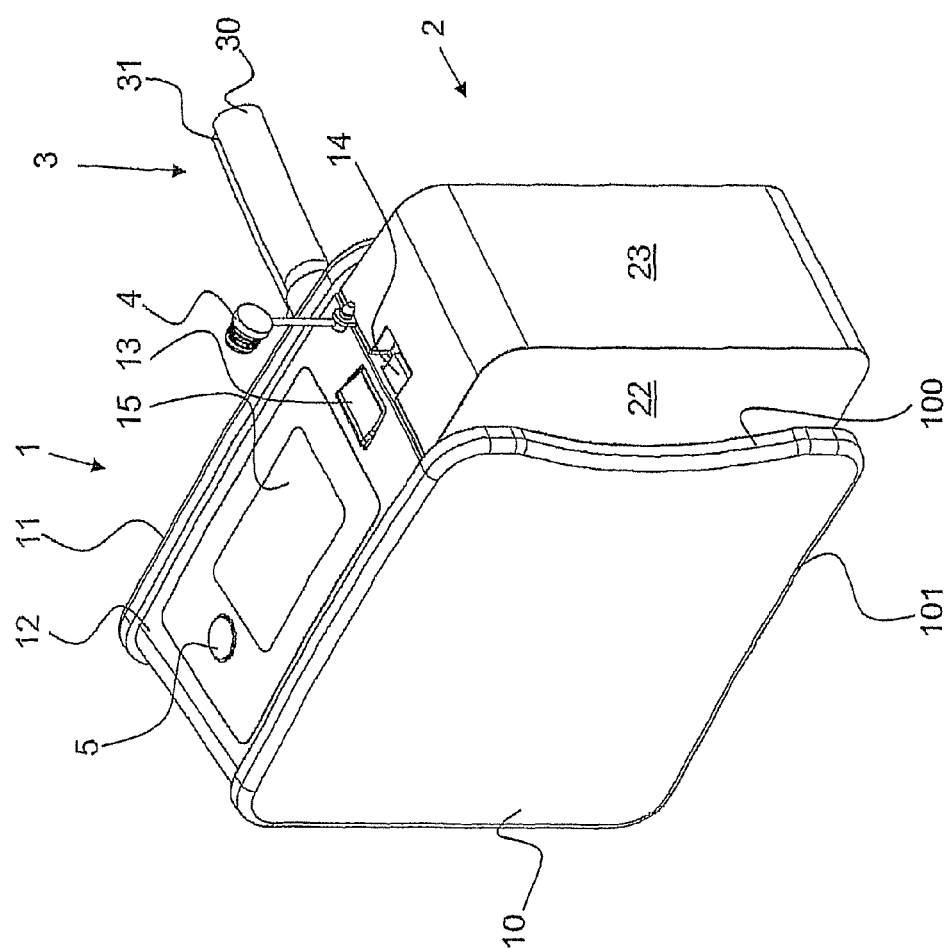
FIG. 1, a perspective view of an aspiration pump unit according to the invention in a first embodiment.
Figure 2:
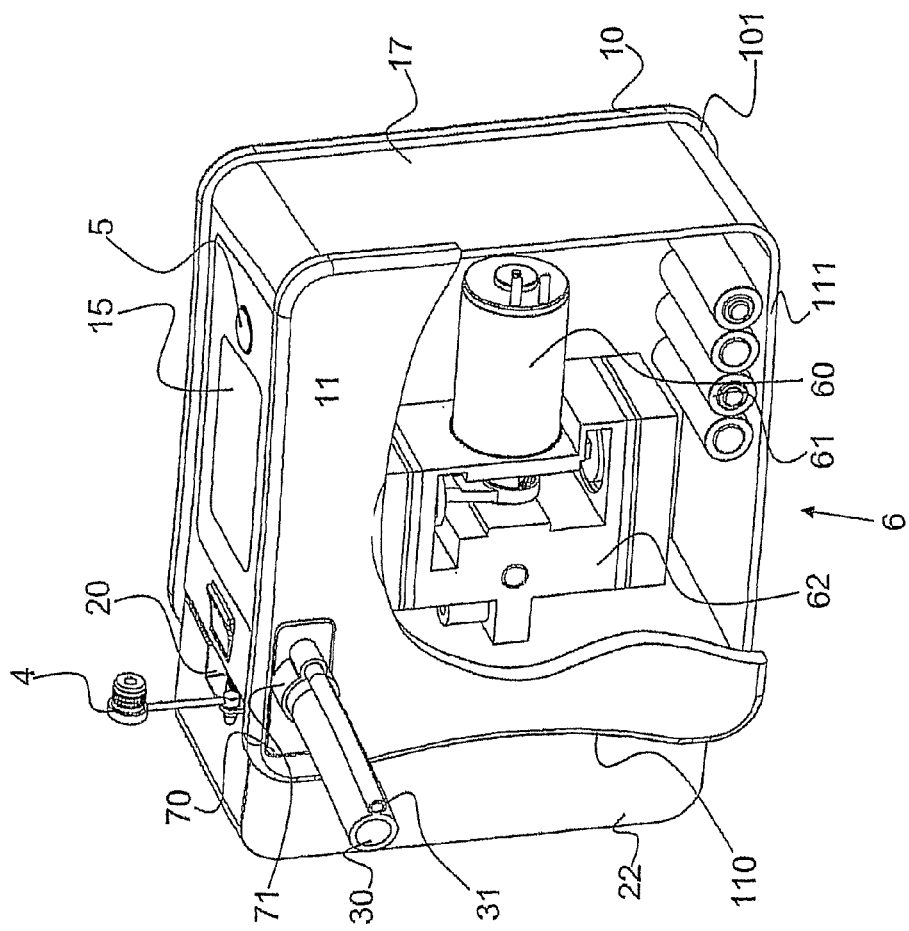
FIG. 2, the aspiration pump unit of FIG. 1, looking into the interior of the housing.

FIGS. 1 and 2 show a first sample embodiment of the invented aspiration pump unit. It consists essentially of a pump assembly housing 1 with a pump assembly 6 arranged therein and visible in FIG. 2 and at least one fluid collection reservoir 2. Preferably, there is exactly one fluid collection reservoir 2 present. The pump assembly 6 serves to create the partial vacuum necessary for the aspiration. The fluid collection reservoir 2 can be connected to the pump assembly 6, so that the partial vacuum can be created in the reservoir 2. The collection reservoir 2 is connected via an aspiration tube or a secretion line 30 to a cavity or wound of the patient, from which it is needed to aspirate the bodily fluid, while the reservoir 2 collects the aspirated bodily fluid.

Preferably, not only the secretion line 30 goes to the patient, but so does a metering line 31, by which the pressure, for example, or the quantity of flow in the secretion line can be measured. For this, preferably, a double-lumen patient tube 3 is used, which contains both lines 30, 31. The tube 3 can be led out in a straight line from the housing 1, as depicted here. However, it can also be arranged with a bend, or one can use a bent adapter piece in which the tube 3 can be inserted.

Figure 7:
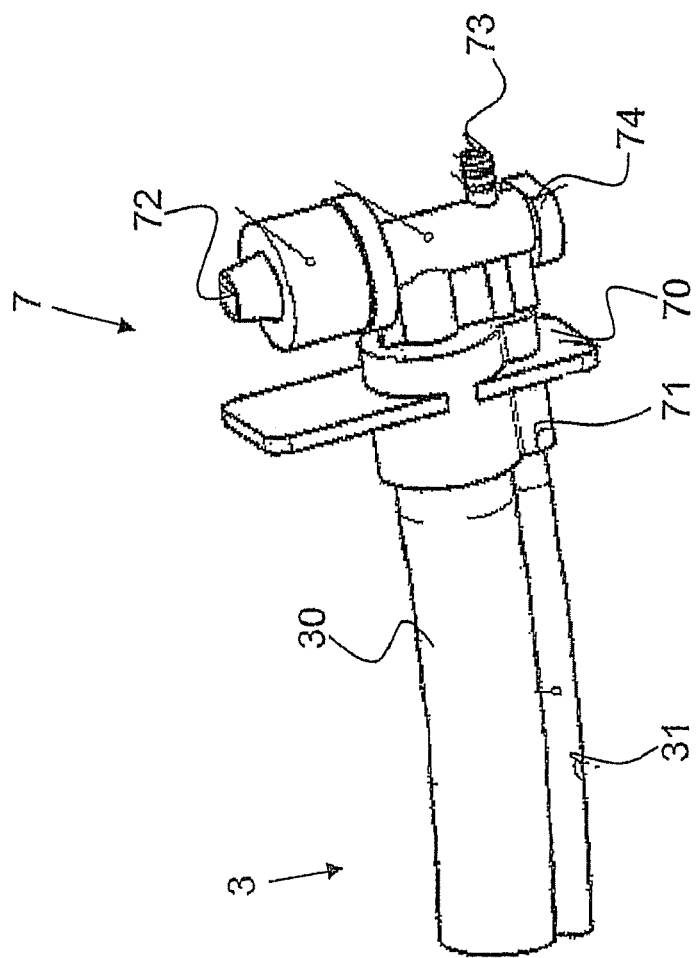
FIG. 7, a perspective representation of an adapter according to the invention, for a tube located at the patient's side.

Preferably, the tube 3 is placed onto an adapter 7. This adapter is shown in detail in FIG. 7. It is preferably made of plastic by means of an injection molding technique. It has a double pipe connector piece 71, on or in which the double-lumen patient's tube 3 can be inserted. A flange 70 is molded on this pipe connector piece 71, which lies against the housing 1 and by means of which the adapter 7 can be secured in the housing 1, for example, by clamping. The part of the adapter 7 inside the housing has a bent coupling piece 72 for a secretion connector 19 at the housing and a connection piece 73 for the metering line 31 or lines. The end 74 opposite the coupling piece 72 is closed.

The pump assembly 6 basically consists of an electric motor 60, a storage element 61, here, batteries, and a vacuum pump 62. The motor 60 is preferably flanged onto the pump 62 and the vacuum pump 62 is preferably secured onto the housing 1. All familiar pumps of sufficiently small size and having enough power for the corresponding application are suitable. The flow rate is preferably around 5 l/min. Preferably, a dual-action membrane pump is used.

The assembly 6 is preferably arranged approximately in the middle or center of the housing 1. It is beneficial for the assembly 6 to be arranged such that the common center of gravity of the housing 1 and the assembly 6 prevents the housing 1 from tilting to the side when one is carrying it.

Figure 3:
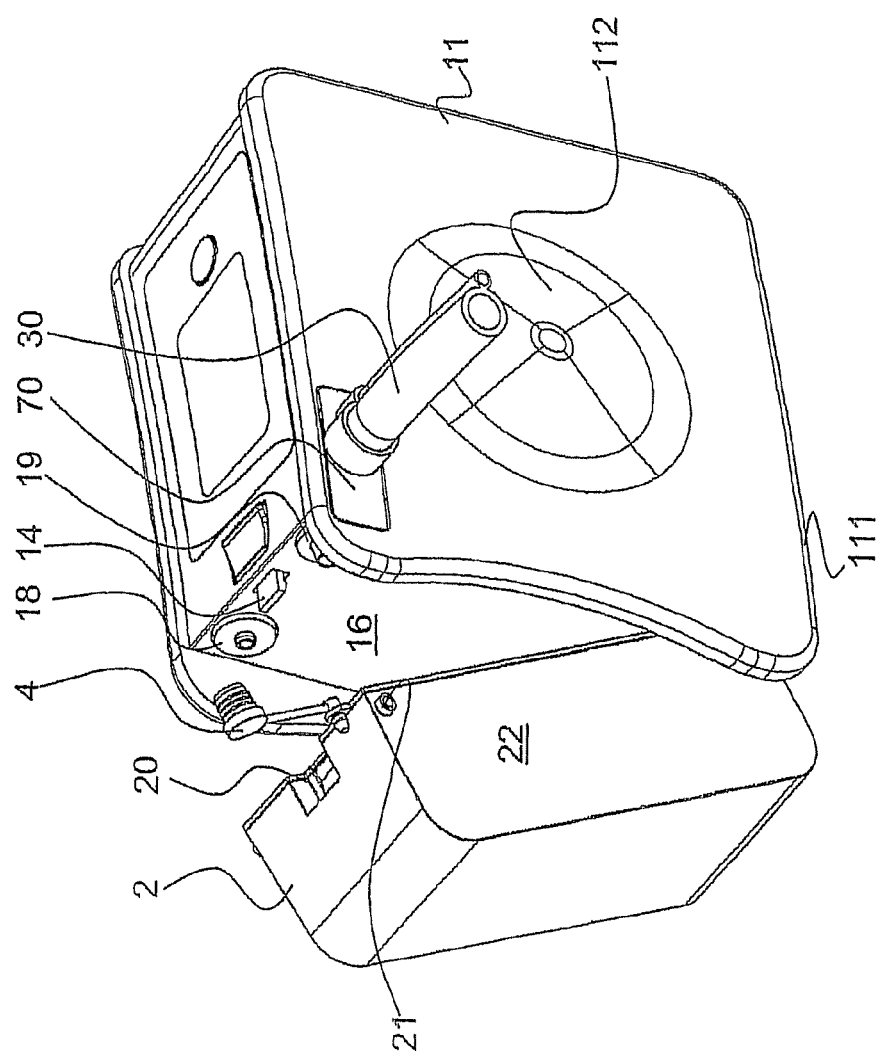
FIG. 3, the aspiration pump unit of FIG. 1 with the fluid collection reservoir partly swiveled out, in perspective view, looking from one side.

The pump assembly housing 1 is essentially shaped as a cuboid, having a rear wall 10, a front wall 11 running approximately parallel to the latter, a first side wall 16 arranged between these walls, a second side wall 17 running approximately parallel to the first side wall 16, and a top wall 12 and a bottom wall not visible in the figure. The housing 1 is preferably made of plastic or metal. The rear wall 10 and the front wall 11 can be configured planar. However, as can be seen in FIG. 3, the front wall 11 can also have a central, outwardly projecting bulge 112. The rear wall 10 can be curved inward, so as to conform to the shape of the human body and thus lie better against the body. The front wall 11 can also be curved accordingly.

Preferably, the rear wall 10 and the front wall 11 have the largest wall surfaces. Furthermore, the top and bottom wall 12 are configured longer than the side walls 16, 17, so that the housing 1 forms a horizontally placed cuboid.

In the figures, the means of fastening for corresponding clamps and straps for carrying the portable aspiration pump unit are not depicted. However, they are preferably located on the rear wall or the side walls of the housing.

Operating elements for the pump assembly 6 are present in the housing 1. These elements are preferably arranged in the top wall 12. In the example depicted here, a main switch 5 is present to turn the unit or the device on and off. Furthermore, there is a display and operating field 15, where status information about the device, the suction process, and other information helpful to an optimal aspiration can be displayed or consulted. For example, the air flow through the secretion line 30 can be metered and presented in the display field 15. It is also possible to arrange a data storage element in the housing 1, in order to save measurement data and show it on the display field 15 by entering proper command instructions.

Furthermore, the vacuum pump 62 or the motor 60 can be activated via this field 15 or desired aspiration parameters can be entered or selected. Preferably, the field 15 is a touchscreen field of familiar kind. However, it is also possible to use, in place of such a field, operating buttons and switches and, optionally, a familiar LCD display. Moreover, these elements can also be arranged in a different wall.

The rear wall 10 and the front wall 11 project by their edges at least beyond the first side wall 16, preferably both side walls and also the bottom and top wall. The field 15 is protected against unintentional activation by the projecting walls 10, 11.

The fluid collection reservoir 2 is likewise approximately cuboid in shape. It has two walls 22 running approximately parallel to each other and being approximately plane, forming the front and rear wall. The same holds for the side walls and the top and bottom wall.

This fluid collection reservoir 2 is held in the housing 1 and can be detached and preferably removed entirely from it. For this, the rear wall 10 and the front wall 11 of the housing have regions, here designated as the front wall edge 110 and rear wall edge 100 that project beyond the first side wall 16. These wall edges 100, 110 are preferably formed curved, having an indentation in their own wall surface. The reservoir 2 is held between these wall edges 100, 110, while the curved regions facilitate the grasping and manual holding of the reservoir 2.

Figure 4:
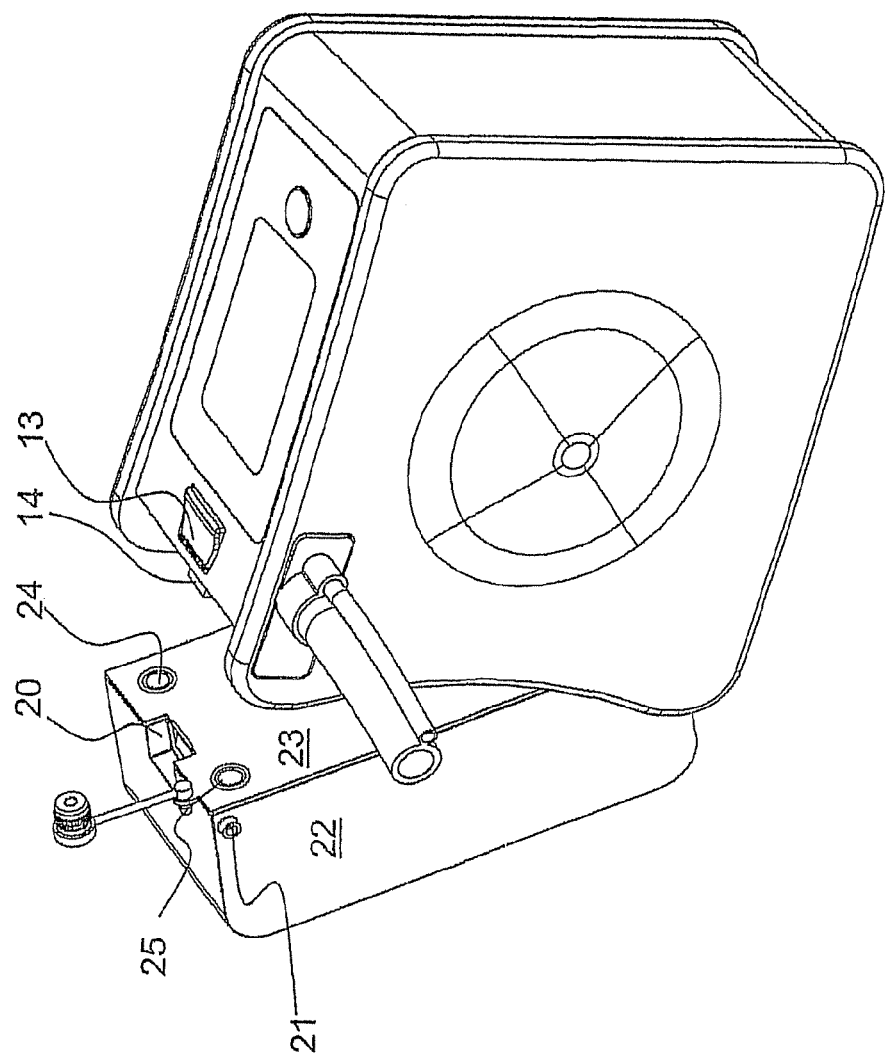
FIG. 4, the aspiration pump unit of FIG. 3 in perspective view looking from a second side.

As can be seen from FIGS. 3 and 4, the reservoir is arranged so that it can be swung in and out between the two edges 100, 110. In its lower region, it is held so that it can swing between the wall edges 100, 110. Preferably, it can be snapped into this position. For this, corresponding bolts are present on the front and rear wall 22 of the reservoir 2 and corresponding recesses are present in the wall edges 100, 110. Of course, the bolts can also be in the wall edges 100, 110 and the recesses in the reservoir 2. Furthermore, other kinds of fastening are also possible, such as allow for a swinging movement and a subsequent removal of the reservoir 2. In at least this region, the shape of the front and rear wall 22 of the reservoir 2 conforms to the shape of the wall edges 100, 110.

The reservoir 2 can be locked to the housing 1 in an upper region. For this, the reservoir 2 has a recess 20, in which a retaining lug 14 of the housing 1 can engage. The retaining lug 14 can be released from engagement with the recess 20 by an unlocking button or switch 13, so that the reservoir 2 can be swung outward. The unlocking button 13 is preferably arranged in the top wall 12. As additional support, the reservoir 2 can be provided with projecting pegs on its front and its rear wall, which are pressed against the wall edges 100, 110, so that the reservoir 2 does not automatically drop out from the device 1 after releasing the locking.

To connect the housing 1 or assembly 6 to the fluid reservoir 2, a vacuum connector 18 at the housing side and the secretion connector 19 at the housing side are arranged in the housing 1, as can be seen from FIG. 3. The pendants at the reservoir side can be seen in FIG. 4. The vacuum connector at the reservoir side is designated 24 and the secretion connector at the reservoir side is designated 25. Both connectors are arranged in a side wall 23 of the reservoir 2. The vacuum connectors 24, 18 for the connection between vacuum pump 62 and reservoir 2. The secretion connectors 19, 25 connect the reservoir 2 to the adapter 7, which can be connected to the secretion line 30.

If the reservoir 2 is removed, the connector 25 at the reservoir side can be closed off by means of a closure element 4. This is preferably fastened to the reservoir 2, as can be seen in FIG. 4. It has a stem and a closure cap arranged at the end of the stem. The closure cap is suitable for closing off the connector 25. The connector 24 can be closed by a filter (not shown), which automatically closes completely when saturated with moisture. Other types of closure are also possible.

In FIG. 2 it can be seen that the projecting edges of the pump assembly housing 1, namely, a back and a front bottom edge 101, 111, form a standing surface for resting on a surface, such as a table. However, the fluid collection reservoir 2 preferably ends with its bottom floor above this standing surface, so that it hangs free in the housing 1. As can be seen from FIG. 5, however, it is held and guided between the two wall edges 100, 110. Furthermore, one can see that the reservoir 2 projects beyond the housing 1 preferably on only a single side.

Figure 5:
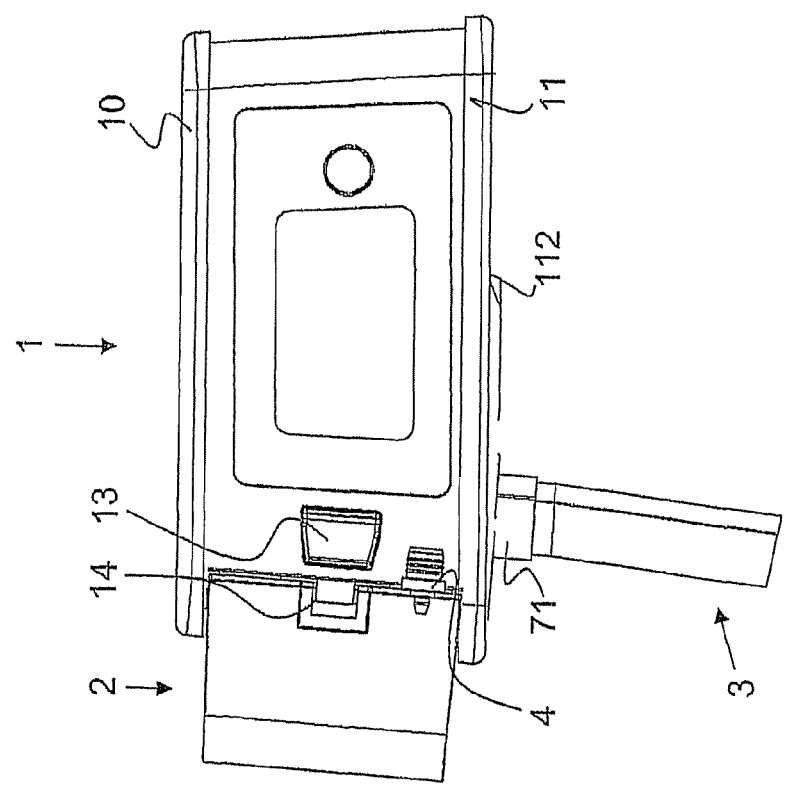
FIG. 5, a top view of the aspiration pump unit of FIG. 1.
Figure 6:
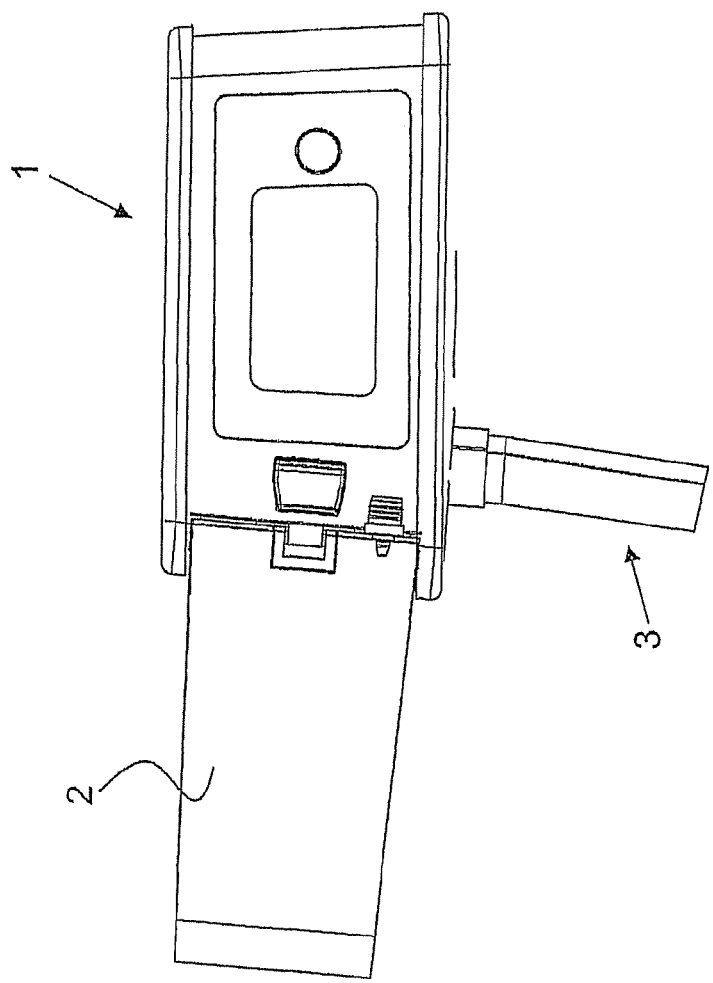
FIG. 6, a top view of the invented aspiration pump unit in a second embodiment.

The size of the reservoir 2 can vary. In FIG. 5, a relatively short reservoir 2 is shown, in FIG. 6 a longer reservoir 2. They need only have the same shape in the region between the wall edges 100, 110, so that they can both be fastened in the same housing 1. The rest of the shape is arbitrary.

Figure 9:
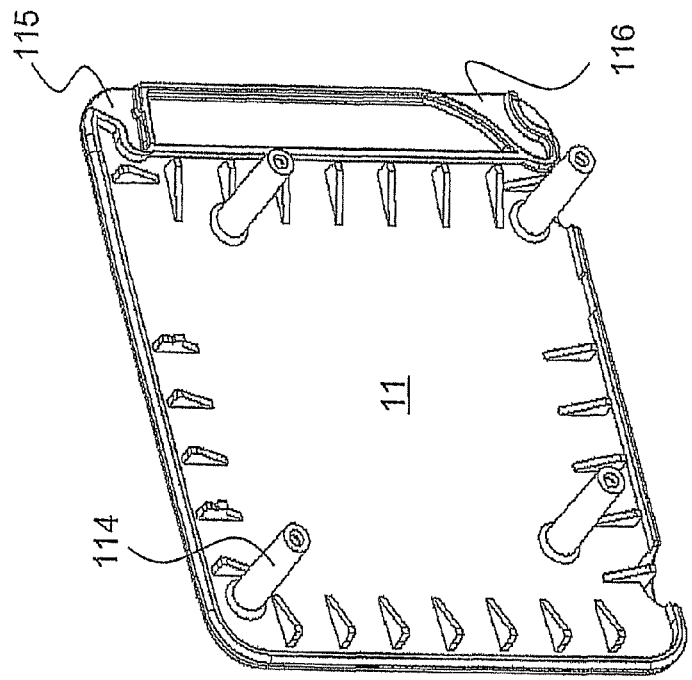
FIGS. 8 and 9, a perspective view of two parts of the housing in a third embodiment.
Figure 8:
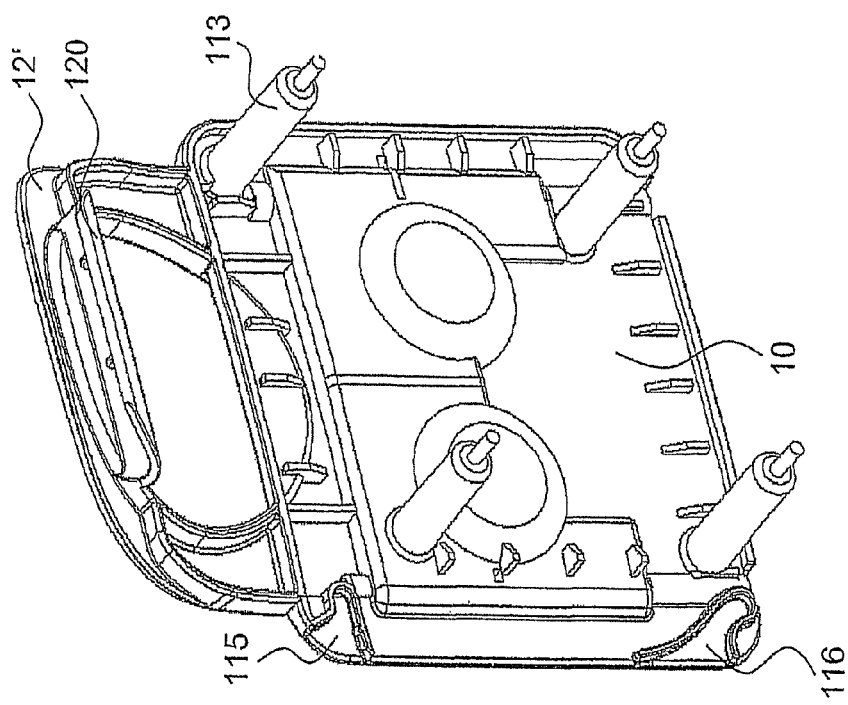

FIGS. 8 and 9 show two opposing parts of a pump assembly housing 1 in a third sample embodiment. These two parts form the rear wall 10 (FIG. 8) and the front wall 11 (FIG. 9) of the housing 1. Both parts are preferably in each case formed in one piece from plastic in an injection molding process.

The two parts 10, 11 are designed such that they can be inserted into one another, with said parts 10, 11 being held spaced apart from one another. For this purpose, perpendicularly projecting insertion mandrels 113, and opposing receiving sleeves 114 which are matched thereto, are arranged at the insides of said parts 10, 11. Said insertion mandrels 113 and receiving sleeves 114 are also preferably injection-molded in one piece with the walls.

One or both of the two walls, here the rear wall 10, can be provided with a handle 12'. A trough 120 is preferably arranged on the handle 12', the bulge of which trough 120 is open in the upward direction. Said trough 120 serves to receive or fasten the patient's tube 30, so that the latter is held so as to be guided along the pump.

At least one part 10, 11, preferably both parts, are provided at their end-side edge with an upper and a lower slotted guide 115, 116. The two opposite upper slotted guides 115 have a widened insertion opening and an adjoining, horizontally-running end region which is aligned inwards away from the edge. The two opposite lower slotted guides 116 likewise have a widened entry region. This however merges, likewise inwards away from the edge, into a lower end region which is aligned obliquely downward. Said slotted guides 115 and 116 serve to hold and retain the fluid collection reservoir 2.

Figure 10:
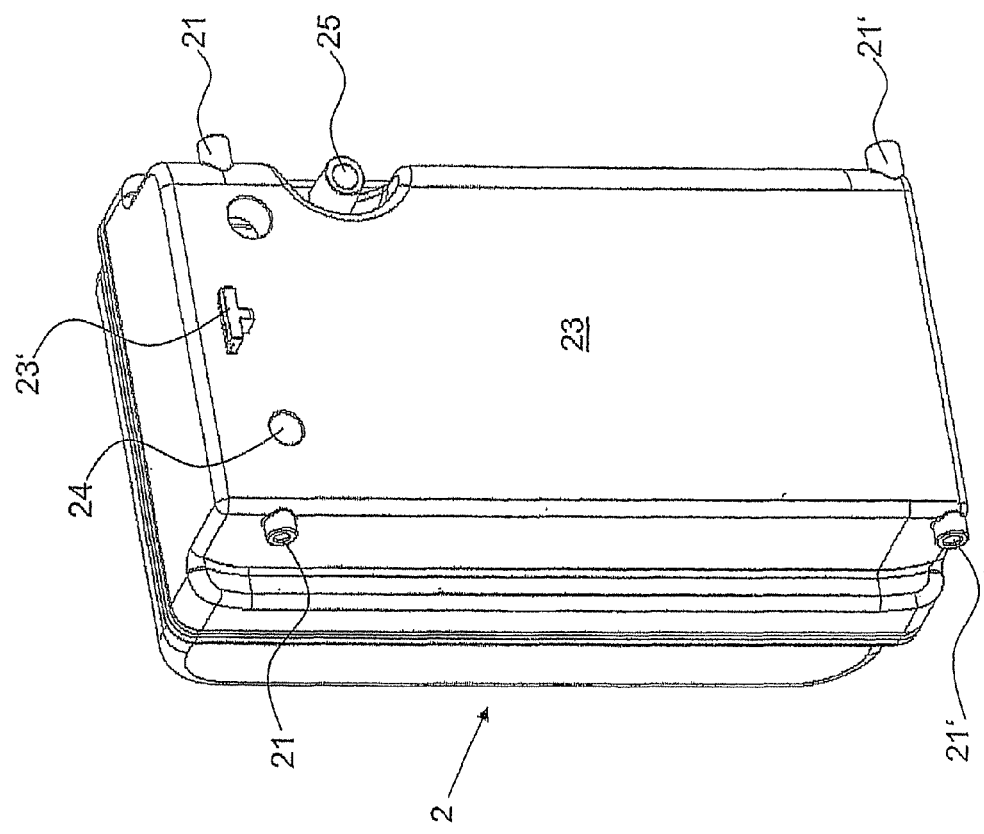
FIG. 10, a perspective view of a fluid collection reservoir suitable for the housing of FIGS. 8 and 9.

A corresponding plastic fluid collection reservoir 2 is shown in FIG. 10. In the region of a side wall 23, said fluid collection reservoir 2 has upper and lower pins or pegs 21, 21' which are integrally injection-molded in one piece onto the rear wall or front wall and project substantially perpendicularly therefrom.

In order to now detachably fasten the collection reservoir 2 to the housing 1, said collection reservoir 2 is first inserted with its lower pins 21' into the lower slotted guide 116 up to the stop, and subsequently snapped with the upper pins 21 into the upper slotted guide 115, or into its end position, by means of a pivoting movement about the pivot axis defined by the end position of the lower slotted guide 116. The same type of fastening is also preferable for the sample embodiments mentioned further above. The pegs can also be arranged on the housing, and the slotted guides on the reservoir. However, other types of fastening are possible.

As can be seen in FIG. 10, in the case of this collection reservoir 2, the vacuum connection 24 at the reservoir and the secretion connection 25 at the reservoir are no longer of the same design as in the sample embodiment above. The adapter piece 70 also need not strictly be arranged in a front or rear wall 10, 11 but can also be arranged at another point of the housing 1, for example in an end side. Furthermore, instead of a recess, the reservoir 2 is provided with an engagement rib 23' for fixing the reservoir 2 to the housing 1, into which engagement rib 23' the retaining lug of the housing 1 can engage. The lug and the recess or rib can also alternatively be arranged on the reservoir or on the housing. These features can be combined with one another in any desired manner, and can also be used in the examples mentioned above.

Figure 12:
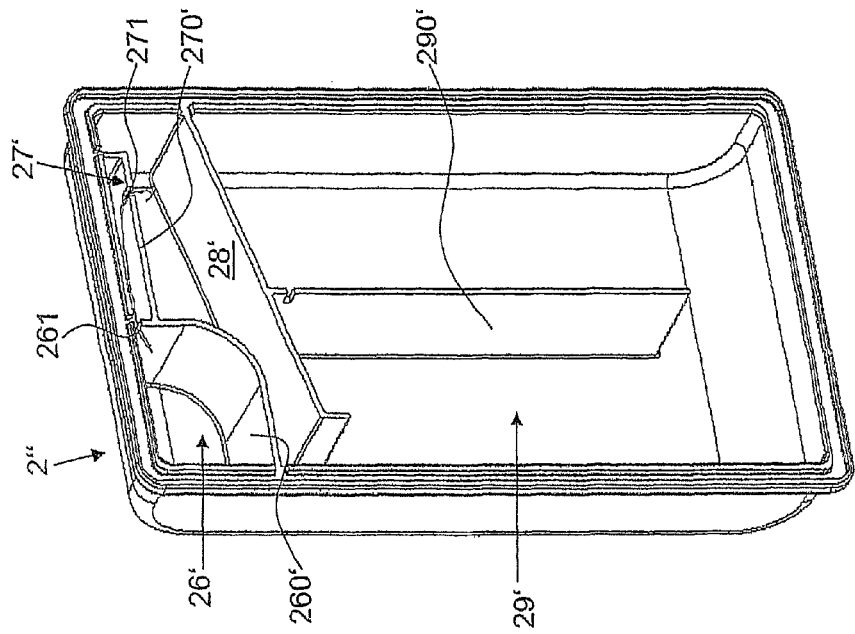
Figure 11:
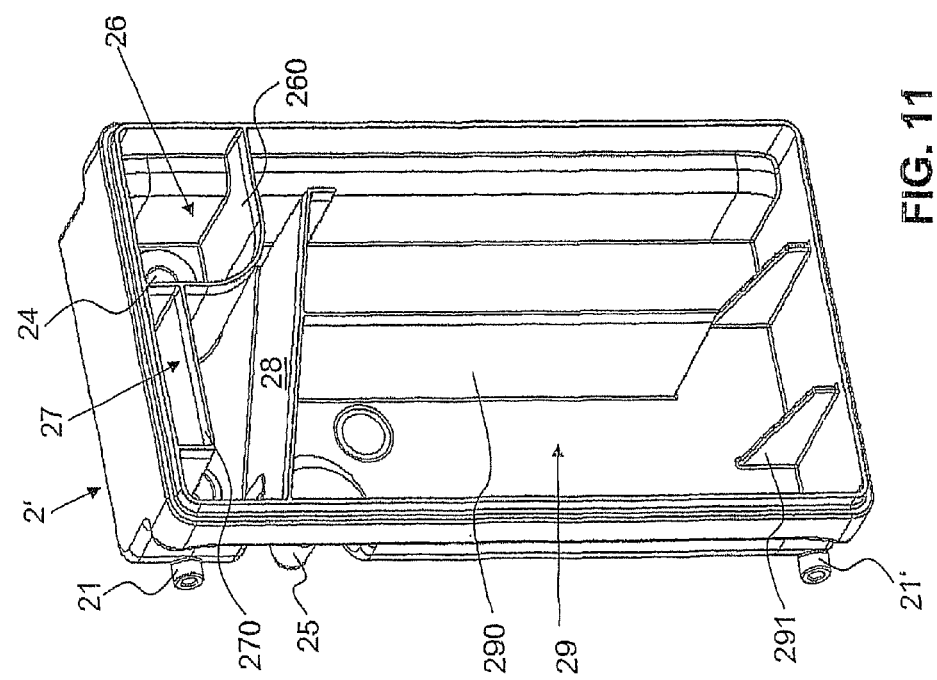
FIG. 11, a perspective view of a first part of the fluid collection reservoir of FIG. 10 and FIG. 12, a perspective view of a second part of the fluid collection reservoir of FIG. 10.

The reservoir 2 can be provided with a single chamber. The interior space of said reservoir 2 is however preferably designed so as to be divided, as shown in FIGS. 11 and 12. This reservoir can be used in all of the sample embodiments. Said reservoir is additionally also suitable for other types of drainage pumps.

The reservoir 2 is composed of two plastic injection-molded parts 2', 2" which are joined to form a common reservoir. Said parts 2', 2" are preferably designed so as to be transparent. The two parts 2', 2" can be plugged together and if appropriate fused to one another. Both parts 2', 2" are provided in the interior space with various ribs, which are described in detail in the following. The two parts 2', 2" have congruent ribs, so that, when said parts 2', 2" are joined together, they form common chambers and regions. The ribs are preferably fused or adhesively bonded to one another when they are joined together, so as to generate an air-tight and liquid-tight connection.

The vacuum connection 24 at the reservoir is arranged in the upper region of the reservoir 2, preferably in the side wall 23 which is provided laterally with the pegs 21, 21' for snapping into the housing 1. The vacuum connection 24 is formed by a continuous opening in said side wall 23. The opening 24 leads into a vacuum chamber 26, 26' which is completely sealingly divided from the rest of the interior space of the reservoir 2 with the exception of a vacuum passage 261. The latter is provided by means of a first curved rib 260 in the first part 2' and a second rib 260', which is of the same shape as said first rib 260, in the second part 2". The passage 261 can be arranged in the first part 2' or, as illustrated here, in the second part 2", or can be arranged at the connecting point of the two ribs 260, 260'. The vacuum passage 261 is preferably arranged in the upper region, adjacent to the upper wall of the reservoir 2.

Following adjacent to this vacuum chamber 26, 26', likewise along the upper wall, is an intermediate chamber 27, 27'. The vacuum passage 261 connects the vacuum chamber 26, 26' to the intermediate chamber 27, 27'. The intermediate chamber 27, 27' is preferably formed by a third rib 270, which is bent at right angles, in the first part 2', and by a congruent rib 270' in the second part 2". Again provided in one of the two parts or in the intermediate region is a passage, referred to here as an intermediate passage 271, which connects the intermediate chamber 27, 27' to the rest of the interior space of the reservoir 2. The intermediate passage 271 is preferably situated in a region remote from the vacuum chamber 26, 26'.

The two passages 261 and 271 are of relatively narrow design. It is however also possible for a plurality of passages to be provided. Said passages should be small enough to prevent as far as possible a return flow of the secretion or of the aspirated fluid, and large enough that the reservoir can be acted on as quickly as possible with the applied vacuum.

Arranged below the intermediate chamber 27, 27' and below the intermediate passage 271 in both parts 2', 2" is in each case one inclined rib 28, 28' which extends downwards from the intermediate passage 271 towards the vacuum chamber 26, 26'. The inclined ribs 28, 28' divide the interior space into an upper and lower region, with the upper region enclosing a significantly smaller volume than the lower region. The inclined ribs (28, 28') preferably extend together over a significant part of the width, but not over the entire width, of the reservoir 2, and over the entire depth of said reservoir 2. In this way, the aspirated fluid must flow downwards along the inclined rib 28, 28'.

The lower region can also be provided with vertically-running dividing ribs 290, 290', 291 which can extend over almost the entire height of the lower region or only over a short lower part thereof.

The secretion connection 25 is arranged in the lower region. The lower region therefore serves to receive the aspirated fluid and forms a secretion chamber 29, 29'. The dividing ribs 290, 290', 291 divide said chamber into sub-chambers which are fluidically connected to one another. Here, however, said sub-chambers prevent the accumulated fluid from surging back and forth. The inclined ribs 28, 28' prevent the fluid spraying into the upper region and, in the event of the reservoir being in a slightly inclined position, prevent the fluid from flowing back into said region. The narrow passage openings and in particular the labyrinth-like arrangement as a result of the intermediate or expansion chamber prevent fluid, which has nevertheless passed into the upper region, from advancing as far as the vacuum connection.

In one embodiment which is not shown, the ribs are arranged in only one part, and the second part is of flat design and serves as a cover.

The intermediate chamber 27, 27' is optional but preferable, since it avoids a direct connection between the vacuum chamber 26, 26' and the secretion chamber 29, 29'.

All of the fluid collection reservoirs described above can be produced in different sizes.

The invented aspiration pump unit enables a simple and secure replacing of the fluid collection reservoir and affords the patient a heightened mobility.

LIST OF REFERENCE NUMBERS 1 pump assembly housing
10 rear wall
100 back wall edge
101 back floor edge
11 front wall
110 front wall edge
111 front floor edge
112 bulge
113 insertion mandrel
114 receiving sleeve
115 upper slotted guide
116 lower slotted guide
12 top wall
12' handle
120 trough
13 release button
14 retaining lug
15 display and operating field
16 first side wall
17 second side wall
18 vacuum connector at housing
19 secretion connector at housing
2 fluid collection reservoir
2' first part
2" second part
20 recess
21 upper peg
21' lower peg
22 rear wall
23 side wall
23' engagement rib
24 vacuum connector at the reservoir
25 secretion connector at the reservoir
26 first part of the vacuum chamber
26' second part of the vacuum chamber
260 first rib
260' second rib
261 vacuum passage
27 first part of the intermediate chamber
27' second part of the intermediate chamber
270 third rib
270' fourth rib
271 intermediate passage
28 first inclined rib
28' second inclined rib
29 first part of the secretion chamber
29' second part of the secretion chamber
290 first long dividing rib
290' second long dividing rib
291 short dividing rib
3 patient's tube
30 secretion line
31 metering line 4 closure element
5 main switch
6 pump assembly
60 motor
61 battery
62 vacuum pump
7 adapter
70 flange
71 pipe connector
72 coupling piece
73 connection piece
74 end

The invention claimed is:

1. A portable aspiration pump unit for the aspiration of bodily fluids and/or air, wherein the aspiration pump unit has
a pump assembly housing with a pump assembly and at least one fluid collection reservoir detachably connected to the pump assembly housing,
wherein the pump assembly housing has a front wall, a rear wall, and a side wall arranged between the front wall and the rear wall,
wherein the front wall and the rear wall each have one wall edge projecting beyond the side wall, and
wherein the fluid collection reservoir
   a) is held between the wall edges,
   b) can swivel in and out between the wall edges in order to mount the reservoir to the housing and to remove the reservoir from the housing,
   c) projects beyond the wall edges when mounted to the housing,
   d) is held and hinged in a lower region between the wall edges and configured to be locked to the pump assembly housing in an upper region, and
   e) has projecting pegs and the housing has lateral slotted guides, the pegs and slotted guides are configured to be placed in engagement with one another.

2. The aspiration pump unit as claimed in claim 1, wherein a retaining lug is provided, which can, by means of an unlocking element, be released from an engagement which fixes the fluid collection reservoir.

3. The aspiration pump unit as claimed in claim 1, wherein the fluid collection reservoir can be snapped into the pump assembly housing in the lower region.

4. The aspiration pump unit as claimed in claim 1, wherein the pump assembly housing has a standing surface for resting on a surface and wherein the fluid collection reservoir terminates with a bottom floor above the standing surface.

5. The aspiration pump unit as claimed in claim 1, wherein the pump assembly housing is formed essentially as a cuboid.

6. The aspiration pump unit as claimed in claim 1, wherein the pump assembly comprises at least a motor and a vacuum pump, wherein the vacuum pump is a membrane pump and wherein the pump assembly is arranged approximately central in the pump assembly housing.

7. The aspiration pump unit as claimed in claim 1, wherein the fluid collection reservoir projects beyond the pump assembly housing on only a single side.

8. The aspiration pump unit as claimed in claim 1, wherein a connector for a patient's tube is arranged in the front wall.

9. The aspiration pump unit as claimed in claim 1, wherein a vacuum connector and a secretion connector are arranged in the side wall of the pump assembly housing.

10. The aspiration pump unit as claimed in claim 1, further including an adapter for a patient's tube, wherein the adapter can be introduced into a wall of the pump assembly housing and the adapter can be connected to the pump assembly and the fluid collection reservoir.

11. The aspiration pump unit as claimed in claim 8, wherein the connector is configured to accommodate a double-lumen patient's tube consisting of a secretion tube and a metering tube.

12. The aspiration pump unit as claimed in claim 10, wherein the adapter is configured to accommodate a double-lumen patient's tube consisting of a secretion tube and a metering tube.

13. The aspiration pump unit as claimed in claim 1, wherein the reservoir can be detached and removed entirely from the housing.

14. The aspiration pump unit as claimed in claim 1, wherein the reservoir is approximately cuboid in shape.

15. The aspiration pump unit as claimed in claim 1, wherein the reservoir comprises a front wall, a rear wall, side walls, a top wall, and a bottom wall.

16. The aspiration pump unit as claimed in claim 1, wherein the housing comprises curved regions which facilitate grasping and manual holding of the reservoir.

\* \* \* \* \*